United States Patent
Tojo (10) Patent No.: US 10,702,351 B2
(45) Date of Patent: Jul. 7, 2020

(54) ROBOT SYSTEM

(71) Applicants: KAWASAKI JUKOGYO KABUSHIKI KAISHA, Kobe-shi, Hyogo (JP); MEDICAROID CORPORATION, Kobe-shi, Hyogo (JP)

(72) Inventor: Tsuyoshi Tojo, Ibaraki (JP)

(73) Assignees: KAWASAKI JUKOGYO KABUSHIKI KAISHA, Kobe-Shi (JP); MEDICAROID CORPORATION, Kobe-Shi (JP)

( * ) Notice: Subject to any disclaimer, the term of this patent is extended or adjusted under 35 U.S.C. 154(b) by 340 days.

(21) Appl. No.: 15/755,465

(22) PCT Filed: Jun. 24, 2016

(86) PCT No.: PCT/JP2016/003064
§ 371 (c)(1),
(2) Date: Feb. 26, 2018

(87) PCT Pub. No.: WO2017/033379
PCT Pub. Date: Mar. 2, 2017

(65) Prior Publication Data
US 2018/0256271 A1 Sep. 13, 2018

(30) Foreign Application Priority Data
Aug. 25, 2015 (JP) .................................. 2015-165479

(51) Int. Cl.
*A61B 34/37* (2016.01)
*G05B 19/418* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
None
See application file for complete search history.

(56) References Cited

U.S. PATENT DOCUMENTS

| 5,116,180 A | 5/1992 | Fung et al. |
| 6,285,379 B1 * | 9/2001 | Gallery .................. G06F 3/011 345/473 |

(Continued)

FOREIGN PATENT DOCUMENTS

| JP | 2008-194789 A | 8/2008 |
| JP | 2009-282720 A | 12/2009 |

OTHER PUBLICATIONS

Aug. 30, 2016 International Search Report issued in International Patent Application No. PCT/JP2016/003064.
(Continued)

*Primary Examiner* — Bhavesh V Amin
(74) *Attorney, Agent, or Firm* — Oliff PLC (57) ABSTRACT

A robot system is provided, which includes a robot body including, robot arm and an end effector attached to robot arm, and operating device, having operating part and configured to output, when operating part is operated, operational information according to operation, a motion controller configured to control operation of robot body according to the operational information outputted from the operating device, a velocity detector configured to detect a velocity at a tip end of the end effector, a virtual reaction-force information generating module configured to output force information containing a first force component having a positive
(Continued)

correlation to the velocity at the tip end of the end effector, as virtual reaction-force information, and a force applying device configured to give a force to the operating part in order to make an operator perceive a force according to the virtual reaction-force information outputted from the virtual reaction-force information generating module.

9 Claims, 7 Drawing Sheets (51) Int. Cl.
| | | |
|---|---|---|
| B23P 19/04 | (2006.01) | |
| B25J 13/00 | (2006.01) | |
| B25J 19/04 | (2006.01) | |
| B25J 9/00 | (2006.01) | |
| B25J 9/16 | (2006.01) | |
| B25J 13/08 | (2006.01) | |
| B25J 3/00 | (2006.01) | |
| B25J 13/06 | (2006.01) | |
| B25J 18/00 | (2006.01) | |
| B25J 19/02 | (2006.01) | |
| B25J 3/04 | (2006.01) | |
| B23Q 15/12 | (2006.01) | |
| B25J 13/02 | (2006.01) | |
| B25J 11/00 | (2006.01) | |
| G06F 3/01 | (2006.01) | |
| H04N 5/232 | (2006.01) | |
| H04N 7/18 | (2006.01) | |
| A61B 34/32 | (2016.01) | |
| G06T 7/62 | (2017.01) | |
| G06T 7/70 | (2017.01) | |
| B23P 21/00 | (2006.01) | |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(56) References Cited

U.S. PATENT DOCUMENTS

| | | | |
|---|---|---|---|
| 7,113,166 | B1* | 9/2006 | Rosenberg ......... A63B 21/0057 345/156 |
| 2009/0216374 | A1 | 8/2009 | Low et al. |
| 2016/0242858 | A1* | 8/2016 | Moctezuma de la Barrera .......... A61B 34/20 |
| 2017/0001301 | A1* | 1/2017 | Kamiya ................. B25J 9/1633 |

OTHER PUBLICATIONS

Bolopion, Aude et al. "A Review of Haptic Feedback Teleoperation Systems for Micromanipulation and Microassembly". IEEE Transactions on Automation Science and Engineering, vol. 10., 496-502 pp. 2013.

Kuchenbecker, Katherine et al. "Induced Master Motion in Force-Reflecting Teleoperation". ASME Journal of Dynamic Systems and Controls, 1-11 pp.

May 2, 2019 Extended Search Report issued in European Patent Application No. 16838731.4.

\* cited by examiner

ROBOT SYSTEM

TECHNICAL FIELD

The present disclosure relates to a robot system.

BACKGROUND ART

Conventionally, technologies utilizing tactile sensing information in robot systems have been known. For example, Patent Document 1 discloses a robot system in which a mobile robot is operated, while obtaining a force sensing feedback between a joy stick and the mobile robot. In recent years, the robot system is applied to various works which require high precision. Examples of application of a master-slave type robot system include a component fitting work, a surgical operation system, etc.

REFERENCE DOCUMENT OF CONVENTIONAL ART

Patent Document

[Patent Document 1] JP2009-282720A

DESCRIPTION OF THE DISCLOSURE

Problem to be Solved by the Disclosure

However, during the work by the conventional robot system, if a force component according to a force received by a slave arm from an object to be worked is presented to a master arm, the master arm itself moves by the force as an operator removes his/her hand from the master arm. Thus, it gives an adverse effect to operability and, as a result, work accuracy decreases. Such a problem is common to a case in which the robot system is applied to a work which requires high precision, such as the component fitting work.

Thus, one purpose of the present disclosure is to enable a highly-precise work in a robot system.

SUMMARY OF THE DISCLOSURE

A robot system includes a robot body including a robot arm and an end effector attached to the robot arm, an operating device having an operating part and configured to output, when the operating part is operated, operational information according to the operation, a motion controller configured to control operation of the robot body according to the operational information outputted from the operating device, a velocity detector configured to detect a velocity at a tip end of the end effector, a virtual reaction-force information generating module configured to output force information containing a first force component having a positive correlation to the velocity at the tip end of the end effector, as virtual reaction-force information, and a force applying device configured to give a force to the operating part in order to make an operator perceive a force according to the virtual reaction-force information outputted from the virtual reaction-force information generating module.

With this configuration, when the operating part is operated by the operator, the operating device outputs operational information according to the operation. The motion controller controls operation of the robot body according to the operational information outputted from the operating device. The velocity detector detects the velocity at the tip end of the end effector attached to the robot arm. The virtual reaction-force information generating module outputs force information containing the first force component having the positive correlation to the velocity at the tip end of the end effector, as the virtual reaction-force information. The force applying device gives the force to the operating part in order to make the operator perceive the force according to the virtual reaction-force information outputted from the virtual reaction-force information generating module. The operator is able to perceive the force according to the virtual reaction-force information given to the operating part. That is, the operator is able to operate the operating part to operate the robot so that the robot suitably performs a work to an object to be worked, while perceiving from the operating part the virtual reaction force of which viscous resistance is exaggerated. Therefore, a highly-precise work is possible.

The robot body may be a slave arm, the operating device may be a master arm, and the slave arm is remotely controlled by the master arm.

The virtual reaction-force information generating module may output force information consisting of the first force component as the virtual reaction-force information.

With this configuration, the force information consisting of the first force component is outputted as the virtual reaction-force information, and the force applying device gives the force to the operating part in order to make the operator perceive a force according to the force information consisting of the first force component. Thus, the operating part does not operate unintentionally even when the operator removes his/her hand from the operating part. Therefore, it does not have a bad influence on the operability.

The virtual reaction-force information generating module may determine whether the velocity at the tip end of the end effector is positive or negative, and output the virtual reaction-force information when the velocity at the tip end of the end effector is positive, and output a value of zero when the velocity at the tip end of the end effector is negative.

With this configuration, when the velocity at the tip end of the end effector is positive, the force applying device gives the force to the operating part according to the virtual reaction force information of which the viscous resistance is exaggerated. On the other hand, when the velocity at the tip end of the end effector is negative, the force applying device gives no force to the operating part. For example, in a case of drawing a surgical instrument out of an incising part in a surgical operation system, since the operator does not perceive the viscous resistance from the surgical instrument, a smooth operation is possible.

The robot body may include a force detecting device configured to detect a force applied to the tip end of the end effector. The virtual reaction-force information generating module may output force information that is obtained by adding a second force component according to the force detected by the force detecting device to the first force component, as the virtual reaction-force information. Here, the force detected by the force detecting device includes forces in each direction of three axis which are perpendicular to each other and moment acting about each axis.

With this configuration, when the force detecting device detects the force applied to the tip end of the end effector, the virtual reaction-force information generating module outputs the force information that is obtained by adding the second force component according to the force detected by the force detecting device to the first force component, as the virtual reaction-force information. Then, the force applying device gives the force to the operating part in order to make the operator perceive the force according to the force information which is consisting of the first and second force components. Here, the force given to the operating part is a force which falls within a range where the movement of the operating part is permitted when the operator removes his/her hand from the operating part. Thus, the operator is able to sense from the operating part the virtual reaction force of which the viscous resistance is exaggerated more.

The force detecting device may be attached to a base end of the end effector, and may be a force sensor configured to detect the force applied to the tip end of the end effector.

The first force component may be a force component proportional to the velocity at the tip end of the end effector.

The robot system may further include a mode selector configured to select, as an operating mode of the motion controller in which operation of the robot body is controlled, any one of an automatic mode in which the operation of the robot body is controlled using a given preset program without reflecting the operational information on the operation of the robot body, a correctable automatic mode in which the operation of the robot body is controlled using the given preset program in the state where the operational information is reflectable on the operation of the robot body, and a manual mode in which the operation of the robot body is controlled using the operational information without using the given program. When the operating mode is the correctable automatic mode, the motion controller may control the robot body so as to perform an operation corrected from the operation related to the given program in response to the operational information while the robot body operates using the given program.

With this configuration, since the automatic mode is selectable by the mode selector as the operation mode of the motion controller, when the operation of the robot is not necessary to be corrected, the automatic mode is selected. In this manner, it is prevented that the operating device is unnecessarily operated to correct the operation. Further, since the manual mode is selectable by the mode selector as the operation mode of the motion controller, the robot main body is operated without using the given program.

The remote control system of the robot may be applied to a surgical operation system, and the end effector may be a surgical instrument.

Effect of the Disclosure

According to the present disclosure, the highly-precise work is enabled in the robot system.

The purpose described above, other purposes, features, and advantages of the present disclosure will be made clear from the following detailed description of suitable embodiments with reference to the accompanying drawings.

MODES FOR CARRYING OUT THE DISCLOSURE

Hereinafter, embodiments according to the present disclosure will be described with reference to the accompanying drawings. Below, the same reference characters are assigned to the same or corresponding components throughout the drawings to omit redundant description.

First Embodiment

Figure 1:
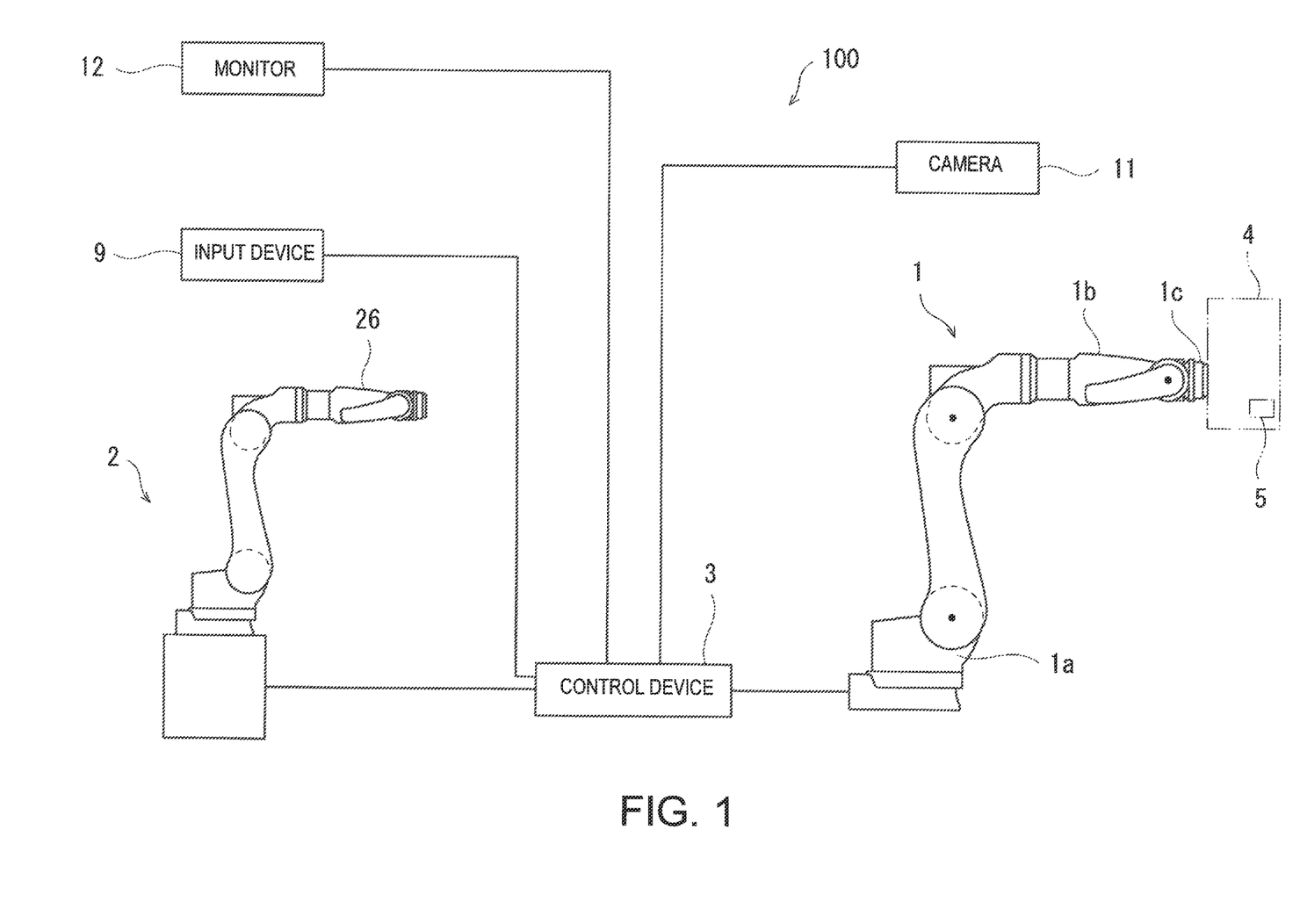
FIG. 1 is a schematic view illustrating one example of a configuration of a robot system according to a first embodiment.

FIG. 1 is a schematic view illustrating one example of a configuration of a robot system according to a first embodiment of the present disclosure. As illustrated in FIG. 1, a robot system 100 of this embodiment is comprised of a master-slave type robot remote control system in which a slave arm 1 is remotely controlled by a master arm 2.

The robot remote control system 100 (hereinafter, simply referred to as "remote control system") includes the slave arm 1 comprised of a first robot, the master arm 2 comprised of a second robot, a control device 3, a force sensor 5, an input device 9, a camera 11, and a monitor 12. The slave arm 1 may be comprised of a robot of any type. The slave arm 1 corresponds to a "robot body" of the present disclosure. In this embodiment, the slave arm 1 is, for example, comprised of a well-known articulated robot, and includes a pedestal 1a, an articulated or multi joint arm 1b provided to the pedestal 1a, and a hand part 1c provided to a tip end of the arm 1b. Each joint of the multi joint arm 1b includes a driving servo motor, an encoder which detects a rotational angular position of the servo motor, and a current sensor which detects current flowing into the servo motor (none of them is illustrated). An end effector 4 is attached to the hand part 1c. The force sensor 5 is attached to the end effector 4.

The master arm 2 may be comprised of a robot of any type. The master arm 2 corresponds to an "operating device" of the present disclosure. The master arm 2 has an operating part 26, and is configured so that, when the operating part 26 is operated, operational information according to the operation is outputted to the control device 3. Although the operating part 26 has a similarity structure to the multi joint arm 1b of the slave arm 1 in this embodiment, the operating part 26 may be a simple device, such as a switch, an adjustment knob, a control lever, or a mobile terminal such as a tablet, or may be a joystick, as long as the operating part 26 is able to operate the slave arm 1 by an operator operating it.

The input device 9 is comprised of man-machine interface(s), such as a touch panel and/or a keyboard. The input device 9 is mainly used in order to input switching of three modes, an automatic mode, a correctable operation mode, and a manual mode of the slave arm 1 (described later), as well as various data. The information inputted into the input device 9 is transmitted to the control device 3.

In the remote control system 100, the operator who is located at a position distant from a workspace of the slave arm 1 (outside the workspace) operates the master arm 2 to input operational information so that the slave arm 1 performs an operation corresponding to the operational information to perform a specific work. Moreover, in the remote control system 100, the slave arm 1 is also capable of automatically performing a given work without the operator operating the master arm 2.

The operating mode in which the slave arm 1 is operated according to the operational information inputted through the master arm 2 is herein referred to as "the manual mode." Note that "the manual mode" also includes a case where part of the operation of the slave arm 1 under operation is automatically corrected based on the operational information inputted by the operator operating the master arm 2. Moreover, the operating mode in which the slave arm 1 is operated according to a given preset program is referred to as "the automatic mode."

Further, the remote control system 100 of this embodiment is configured to be correctable of the operation of the slave arm 1 which is to be performed automatically, by reflecting the operation of the master arm 2 on the automatic operation of the slave arm 1, while the slave arm 1 operates automatically. The operating mode in which the slave arm 1 is operated according to the given preset program in a state where the operational information inputted through the master arm 2 is reflectable is herein referred to as a "correctable automatic mode." Note that "the automatic mode" described above is distinguished from "the correctable automatic mode" in that the operation of the master arm 2 is not reflected on the operation of the slave arm 1 when the operating mode in which the slave arm 1 is operated is the automatic mode.

The camera 11 is provided so as to be able to image the operation of the slave arm 1 in all or part of a movable range of the slave arm 1. The image information imaged by the camera 11 is transmitted to the control device 3, and the control device 3 then controls the monitor 12 to display an image corresponding to the image information.

Figure 2:
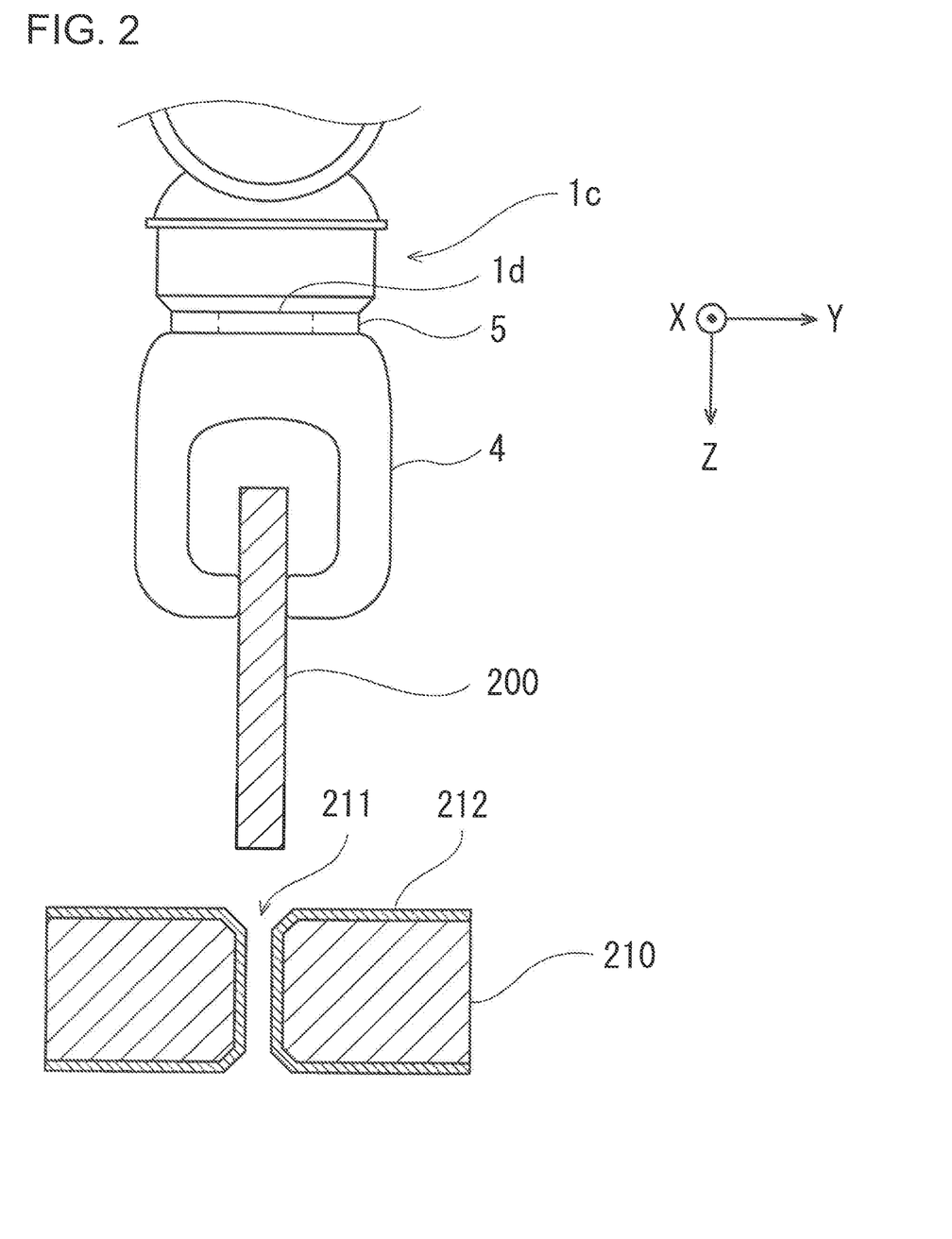
FIG. 2 is a schematic view illustrating one example of a configuration at a tip end of a slave arm of FIG. 1.

FIG. 2 is a schematic view illustrating one example of a configuration of a tip end of the slave arm 1. As illustrated in FIG. 2, the end effector 4 is attached to an attachment surface 1$d$ at the tip end of the hand part 1$c$. In this embodiment, the end effector 4 is a robot hand which is capable of gripping a fitting component 200. The robot hand includes a hand main body attached to the attachment surface 1$d$ at the tip end of the hand part 1$c$, and two finger parts driven by an actuator (not illustrated), for example, comprised of a motor. When the actuator operates, the two finger parts move with respect to the hand main body. That is, the two finger parts of the robot hand are movable so as to approach or separate mutually, and are capable of gripping the fitting component 200. In the remote control system 100 of this embodiment, a shaft (200) held by the robot hand (4) is inserted into a hole (211) of a gear (210) by the operation of the slave arm 1. Lubricating oil 212 is applied to the surface and the side surface of the hole (211) of the gear (210). Since high precision is required for this work, this work requires a skilled operator among assembly operations.

The force sensor 5 is attached between the attachment surface 1$d$ at the tip end of the hand part 1$c$, and the end effector 4. The force sensor 5 corresponds to a "force detecting device" of the present disclosure. In this embodiment, the force sensor 5 is attached to a base end of the end effector 4, and it is configured to detect a force applied to the tip end of the end effector 4. In this embodiment, the force sensor 5 is a 6-axis force sensor capable of detecting forces in XYZ-axes directions defined by a hand part coordinate system, and moment acting about each axis. Here, the hand part coordinate system is a coordinate system on the basis of the hand part 1$c$. In FIG. 2, the X-axis and the Y-axis are defined in parallel with the attachment surface 1$d$ of the hand part 1$c$, and the Z-axis is defined in a direction perpendicular to the attachment surface 1$d$. The force sensor 5 transmits wirelessly or wiredly a detection signal to the control device 3.

Figure 3:
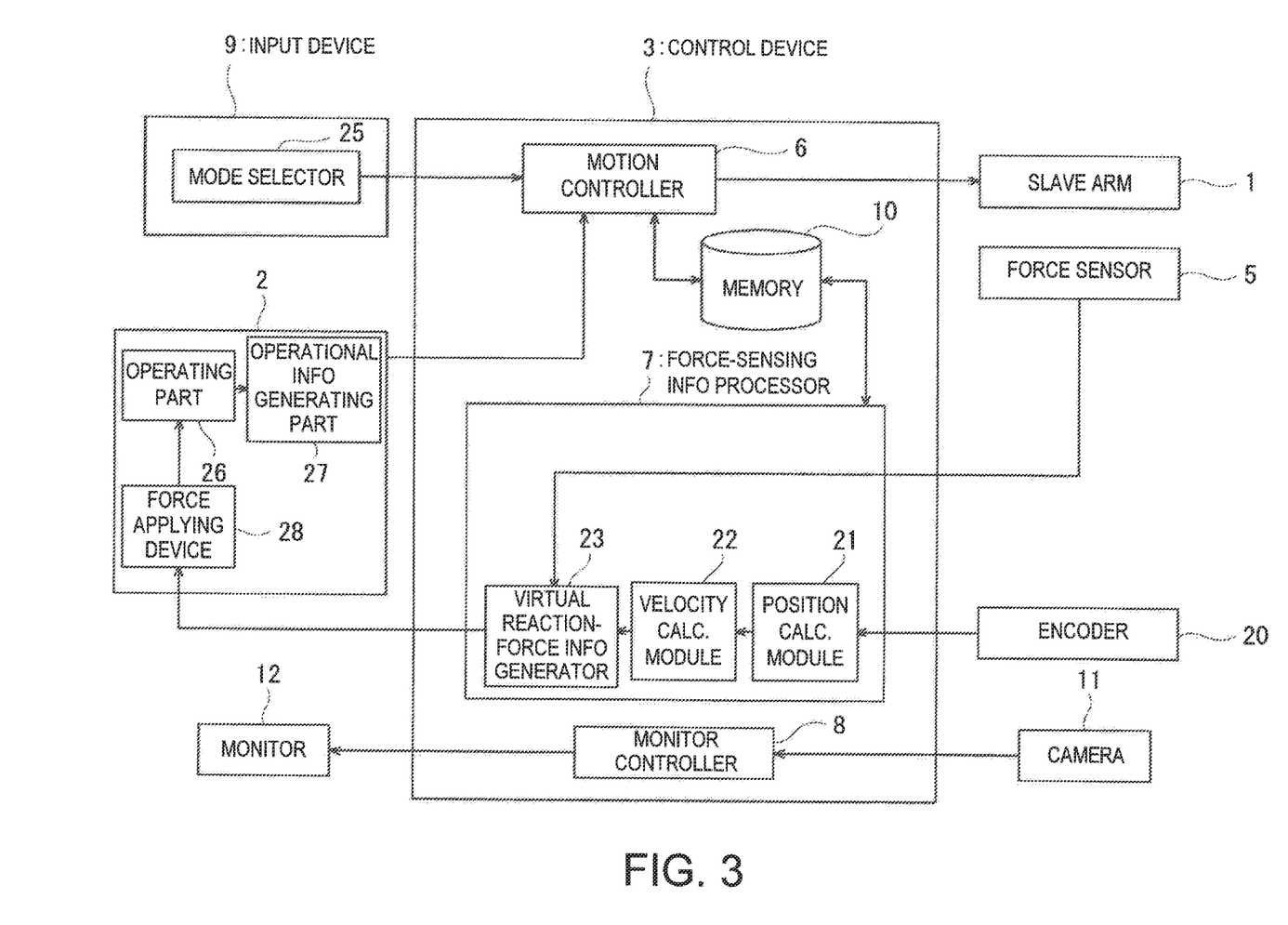
FIG. 3 is a block diagram illustrating a configuration of a master arm and a control device of FIG. 1.

FIG. 3 is a block diagram illustrating a configuration of the master arm 2 and the control device 3. As illustrated in FIG. 3, the master arm 2 includes the operating part 26, an operational information generating part 27, and a force applying device 28. The operating part 26 is comprised of the multi joint arm similar to the slave arm 1 (see FIG. 1), and it is operated by the operator and a force (torque) is given to each joint shaft by the force applying device 28. The operational information generating part 27 is configured so that it generates, when the operating part 26 is operated by the operator, the operational information according to this operation, and outputs it to a motion controller 6. The force applying device 28 is configured to give a force (torque) to each joint shaft of the multi joint arm (the operating part 26).

The control device 3 includes the motion controller 6, a force-sensing information processor 7, a monitor controller 8, a memory 10, and an interface part (not illustrated). The control device 3 is comprised of a device having arithmetic processing capabilities, such as a computer, a micro controller, and a microprocessor. The motion controller 6, the force-sensing information processor 7, and the monitor controller 8 are implemented by an operation processor (not illustrated) of the control device 3 executing given program(s) stored in the memory 10 of the control device 3. The hardware configuration of the control device 3 may be arbitrary, and the control device 3 may be provided separately from other devices, such as the slave arm 1, or may be provided integrally with other devices.

The motion controller 6 controls the operation of the slave arm 1 according to the operational information transmitted from the master arm 2 and the information inputted from the input device 9. Here, a mode selector 25 of the input device 9 is for the operator to select any one of "the automatic mode," "the correctable automatic mode," and "the manual mode" which are described above as the operating mode in which the slave arm 1 is operated. The information related to the mode selected by the operator is inputted into the motion controller 6 from the mode selector 25. The memory 10 is a readable and writable recording medium, which stores beforehand the given program(s) and various data for causing the slave arm 1 to automatically perform the given operation. The given program is, for example, instruction information which is stored by an instruction work in which the slave arm 1 is operated to perform the given work. In this embodiment, the instruction information may be information stored by instructing the operation of the slave arm 1 by operating the master arm 2, or may be information stored by a direct instruction. Note that, although the memory 10 is provided integrally with the control device 3, it may be provided separately from the control device 3. Specifically, the motion controller 6 controls the servo motor which drives each joint shaft of the slave arm 1 based on at least one of the operational information from the master arm 2 and the prestored information. The motion controller 6 generates a positional instruction value of each joint shaft of the slave arm 1, and generates a velocity instruction value based on a difference between the generated positional instruction value and the detection value (actual value) of the encoder. Then, the motion controller 6 generates a torque instruction value (current instruction value) based on the difference between the generated velocity instruction value and a present velocity value, and controls the servo motor based on a difference between the generated current instruction value and a detection value (actual value) of the current sensor.

The force-sensing information processor 7 includes a position calculating module 21, a velocity calculating module 22, and a virtual reaction-force information generating module 23.

The position calculating module 21 is capable of acquiring the detection signal of the encoder 20, and identifying the position and posture of the hand part 1c of the slave arm 1 in a common base coordinate system based on the rotational angular position of each joint shaft of the slave arm 1, and dimensions of links which constitute the slave arm 1. Then, the position calculating module 21 calculates the position at the tip end of the end effector 4 on the basis of the base coordinate system by storing beforehand a vector from the position of the hand part 1c to the tip end of the end effector 4 in the hand part coordinate system on the basis of the hand part 1c, and outputs it to the velocity calculating module 22. Note that the remote control system 100 may have a measuring device (not illustrated) capable of measuring an arbitrary point on space and generating coordinate data of the point, and the position calculating module 21 may convert the coordinate data of the measured point from a given coordinate system of the measuring device to the base coordinate system to calculate the position at the tip end of the end effector 4 on the basis of the base coordinate system.

The velocity calculating module 22 acquires the position at the tip end of the end effector 4 outputted from the position calculating module 21, calculates a velocity component at the tip end of the end effector 4 based on an amount of movement at a given time interval, and outputs it to the virtual reaction-force information generating module 23.

The virtual reaction-force information generating module 23 acquires the detection signal of the force sensor 5, and the velocity component at the tip end of the end effector 4 calculated by the velocity calculating module 22, generates virtual reaction-force information based on the information, and outputs it to the master arm 2. Here, the virtual reaction-force information generating module 23 determines whether the force applied to the tip end of the end effector 4 increases with time based on the detection signal of the force sensor 5. If the force applied to the tip end of the end effector 4 increases, the virtual reaction-force information generating module 23 outputs force information containing a first force component having a positive correlation to the velocity at the tip end of the end effector 4 to the force applying device 28 as the virtual reaction-force information. The virtual reaction-force information generating module 23 outputs a value of zero to the force applying device 28 if the force applied to the tip end of the end effector 4 decreases with time.

The force applying device 28 gives a force to the operating part 26 in order to make the operator perceive the force corresponding to the virtual reaction-force information outputted from the virtual reaction-force information generating module 23. Here, synthetic reaction-force information is converted into a torque value to each joint shaft of the master arm 2 (the operating part 26). For example, the converted torque value corresponds to a torque instruction to a driver circuit of the servo motor which drives each joint.

The monitor controller 8 controls the monitor 12 to display the image corresponding to the image information which is imaged by the camera 11. The operator is able to operate the slave arm 1 as he/she intended by operating the master arm 2 (the operating part 26) while looking at the monitor 12.

Operation

Figure 4:
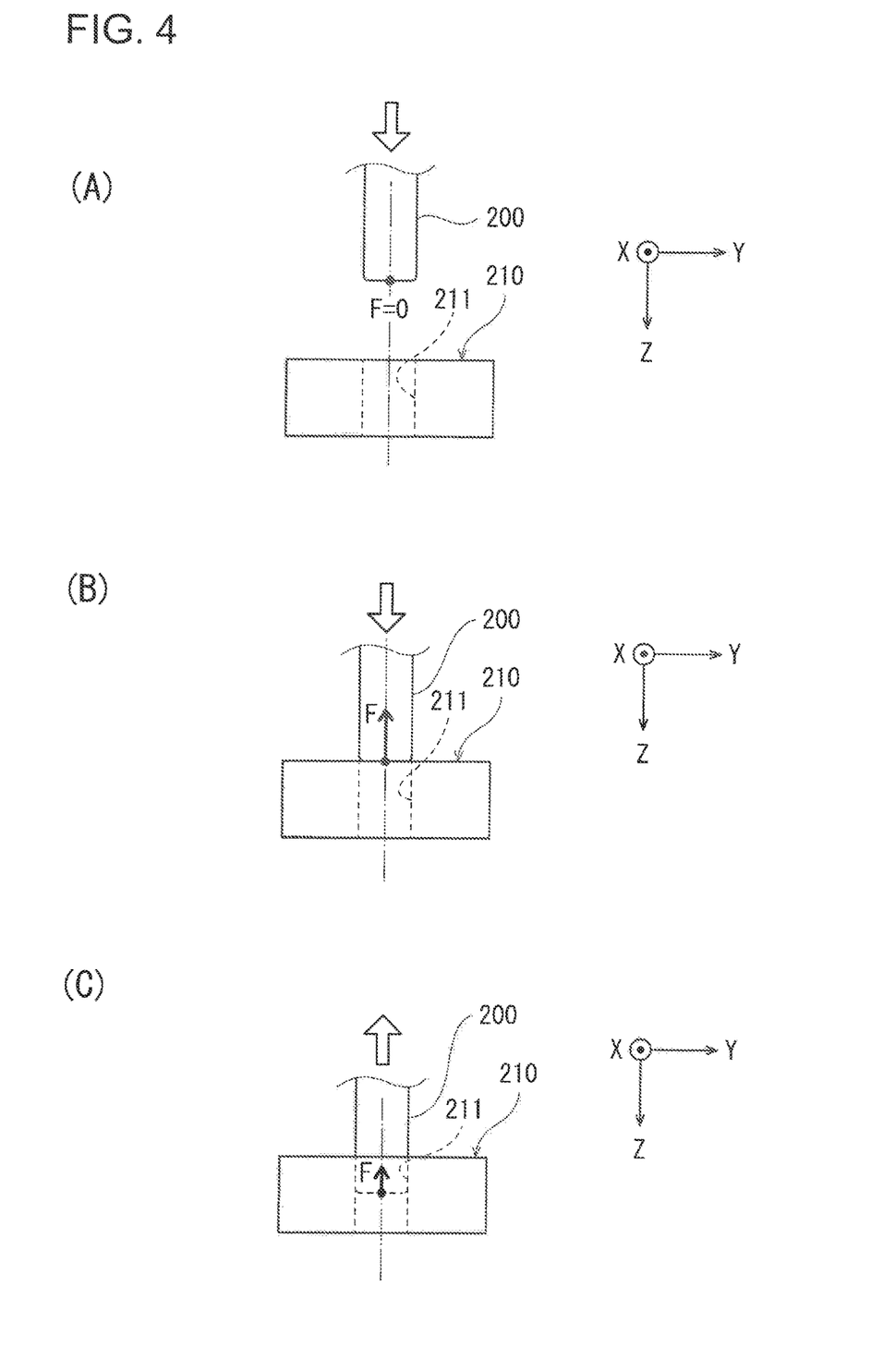
FIG. 4 is a view schematically illustrating a force acting on a tip end of a robot hand of FIG. 2 according to a work stage.

Next, operation of the remote control system 100 is described using FIGS. 2 to 4. In the remote control system 100 of this embodiment, the shaft (200) held by the robot hand (4) is inserted into the hole (211) of the gear (210) by the operation of the slave arm 1 (see FIG. 2). Here, a case where the operating mode selected by the operator with the mode selector 25 is "the manual mode" is described. The motion controller 6 controls the operation of the slave arm 1 according to the operational information (inputted instruction) sent by operating the master arm 2 without using the given program, when the operating mode in which the slave arm 1 is operated is "the manual mode" (see FIG. 3).

FIG. 4 is a view schematically illustrating the force acting on the tip end of the robot hand (4) according to a work stage. First, as illustrated in FIG. 4(A), the operator operates the master arm 2 (the operating part 26) while looking at the monitor 12 to depress the robot hand (4) which grips the shaft (200) in a direction toward the gear (210) (in this figure, the positive Z-axis direction) by the operation of the slave arm 1. Here, the centerline of the shaft (200) is controlled so as to be aligned with the centerline of the hole (211) of the gear (210). In this embodiment, a contact determination of whether the tip end of the shaft (200) contacts the gear (210) is performed based on the detection signal of the force sensor 5. Since no force is applied to the tip end of the robot hand (4) until the tip end of the shaft (200) contacts the gear (210), a force value detected by the force sensor 5 is zero. Note that, in this embodiment, since the shaft (200) is gripped by the robot hand (4), the force applied to the tip end of the shaft (200) gripped by the robot hand (4) is about the same as the force applied to the tip end of the robot hand (4).

Next, as illustrated in FIG. 4(B), when the tip end of the shaft (200) contacts the gear (210), the operator starts the work in which the shaft (200) is inserted into the gear (210) by the operation of the slave arm 1, by operating the master arm 2 while looking at the monitor 12. When the force sensor 5 attached to the tip end of the slave arm 1 detects the force F applied to the tip end of the robot hand (4), the virtual reaction-force information generating module 23 determines whether the force F applied to the tip end of the end effector 4 increases with time based on the detection signal of the force sensor 5. In FIG. 4(B), when the tip end of the shaft (200) contacts the surface of the gear (210) or the side surface of the hole (211), it receives the force in the negative Z-axis direction. In this case, since the force applied to the tip end of the robot hand (4) increases with time, the virtual reaction-force information generating module 23 outputs force information containing the first force component having the positive correlation to the velocity at the tip end of the robot hand (4) as virtual reaction-force information P(t) to the master arm 2 (the force applying device 28), as illustrated in Equation (1).

$$P(t) = (K \times (dr/dt)) \times h(t) \qquad (1)$$

Here, r represents the position at the tip end of the robot hand (4), t represents time, and K represents a factor of proportionality. h(t) represents a unit step function illustrated in Equation (2). F represents the force applied to the tip end of the robot hand (4).

$$h(t)=1(dF/dt \leq 0), h(t)=0(dF/dt<0) \qquad (2)$$

According to Equation (1), the first force component having the positive correlation to the velocity at the tip end of the robot hand (4) is a force component proportional to the velocity component at the tip end of the robot hand (4). That is, the virtual reaction-force information generating module 23 converts the velocity component dr/dt at the tip end of the robot hand (4) into an appropriate range, and outputs it to the force applying device 28 of the master arm 2 as the virtual reaction-force information. Note that noise component of the virtual reaction-force information may be removed by a low pass filter (not illustrated).

The force applying device 28 gives a force to the master arm 2 (the operating part 26) in order to make the operator perceive the force according to the virtual reaction-force information outputted from the virtual reaction-force information generating module 23. The operator is able to perceive the force according to the virtual reaction-force information given to the operating part 26. That is, the operator is able to operate the operating part 26 so that the shaft (200) is inserted by the operation of the slave arm 1, into the gear (210) to which the lubricating oil (212) is applied, while perceiving from the operating part 26 the virtual reaction force of which viscous resistance is exaggerated. Therefore, a highly-precise work is possible.

Moreover, since the force applying device 28 gives the force to the operating part 26 in order to make the operator perceive the force according to the force information which is consisting of the first force component (see Equation (1)), the operating part 26 does not operate unintentionally even when the operator removes his/her hand from the operating part 26. Therefore, it does not have a bad influence on the operability.

On the other hand, as illustrated in FIG. 4(C), the operator may draw out a tip-end part of the once-inserted shaft (200) from the hole (211) during the work. Since the lubricating oil (212) is applied to the inside of the hole (211), the tip end of the shaft (200) receives a force in the minus Z-axis direction. In this case, the force F applied to the tip end of the shaft (200) (the negative Z-axis direction) decreases, compared with the case of FIG. 4(B). As a result, since the force applied to the tip end of the robot hand (4) decreases with time, the virtual reaction-force information generating module 23 outputs the value of zero to the force applying device 28 of the master arm 2. As a result, the force applying device 28 gives no force to the operating part 26. Since the operator does not perceive the viscous resistance from the operating part 26, a smooth operation is possible.

Note that, in this embodiment, although the virtual reaction-force information generating module 23 outputs the force information containing the first force component having the positive correlation to the velocity at the tip end of the robot hand (4) as the virtual reaction-force information (see Equation (1)), the present disclosure is not limited to this configuration. As illustrated in Equation (3), the virtual reaction-force information generating module 23 may output force information which is obtained by adding a second force component according to the force detected by the force sensor 5 to the first force component as the virtual reaction-force information P(t).

$$P(t)=(K\times(dr/dt))\times h(t)+f(t) \quad (3)$$

Here, f(t) represents the second force component according to the force detected by the force sensor 5. Thus, the operator is able to sense from the operating part 26 the virtual reaction force of which the viscous resistance is exaggerated.

Note that, upon generating the second force component f(t), the virtual reaction-force information generating module 23 converts the force applied to the tip end of the robot hand (4) detected by the force sensor 5 into the appropriate range to set the force given to the operating part 26 as a force which falls within a range where the movement of the operating part 26 is permitted when the operator removes his/her hand from the operating part 26.

Note that, in this embodiment, although the virtual reaction-force information generating module 23 outputs the value of zero when the force applied to the tip end of the robot hand (4) decreases (see Equation (1)), it may output the value of zero when an absolute value of the force is smaller than a given value.

Figure 5:
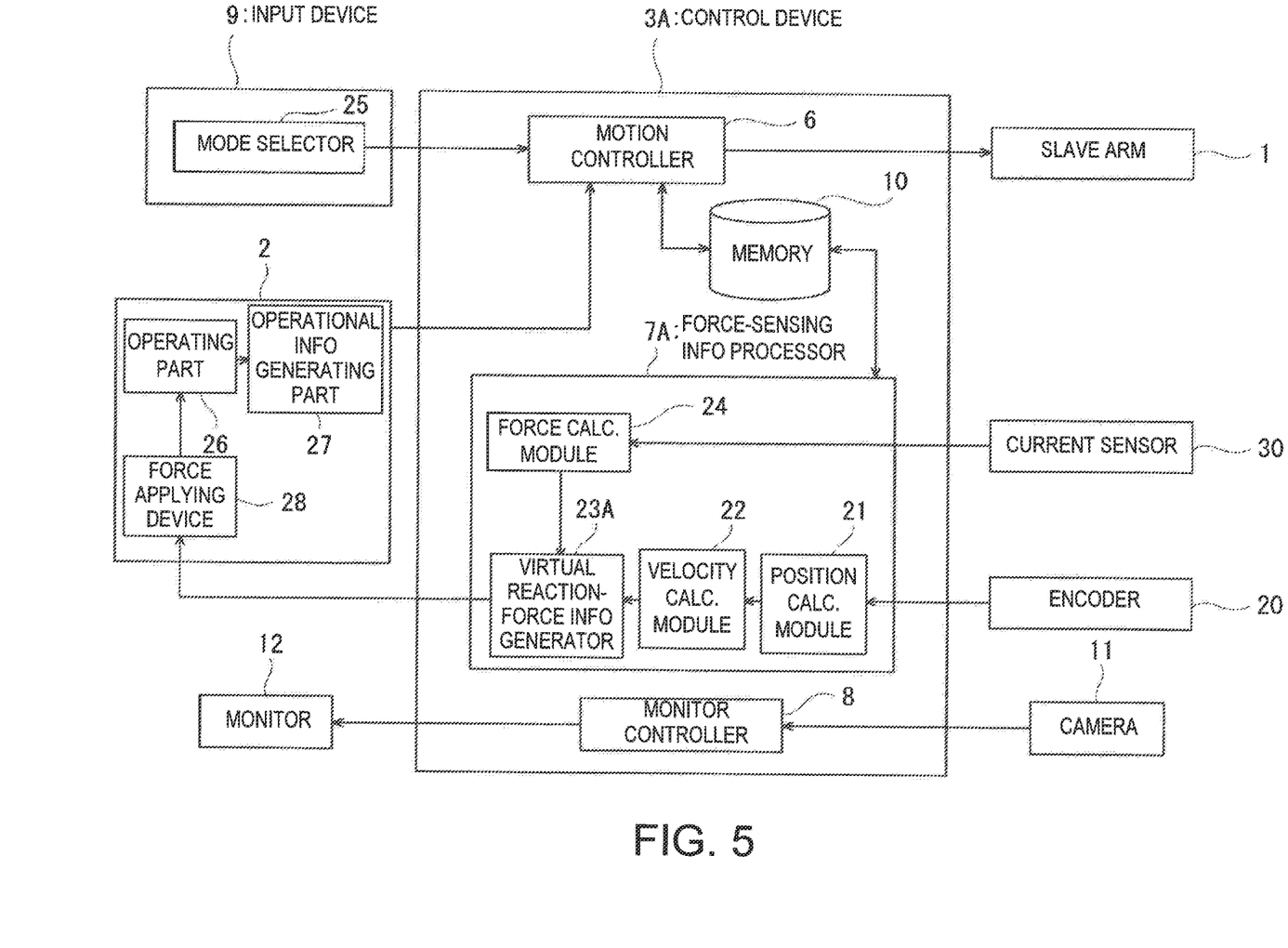
FIG. 5 is a block diagram illustrating a configuration of a master arm and a control device of a robot system according to a modification of the first embodiment.

FIG. 5 is a block diagram illustrating a configuration of a control device 3A of a remote control system of a robot according to a modification of this embodiment. As illustrated in FIG. 5, the remote control system of this modification differs from this embodiment in that it is not provided with the force sensor 5 (see FIG. 3). A force-sensing information processor 7A is further provided with a force calculating module 24. Although the force calculating module 24 acquires from the current sensor 30 a value of current flowing into the servo motor which drives each joint shaft of the slave arm 1, and calculates the force acting on the tip end of the end effector 4 of the slave arm 1 based on a rate of change in a difference between the current instruction value and the detection value of the current sensor 30, it may calculate the force acting on the tip end of the end effector 4 of the slave arm 1 based on a rate of change in a positional deviation or velocity deviation of each joint shaft. In this modification, a virtual reaction-force information generating module 23A determines whether the tip end of the shaft (200) contacts the gear (210) based on an output signal of the force calculating module 24. Moreover, the virtual reaction-force information generating module 23A generates virtual reaction-force information only based on the velocity at the tip end of the robot hand (4). The virtual reaction-force information generating module 23A determines whether the velocity at the tip end of the robot hand (4) is positive or negative, and according to Equations (1) illustrated above and (4), outputs the virtual reaction-force information P(t) when the velocity at the tip end of the robot hand (4) is positive, and outputs the value of zero when the velocity at the tip end of the robot hand (4) is negative.

$$P(t)=(K\times(dr/dt))\times h(t) \quad (1)$$

$$h(t)=1(dr/dt\leq 0), h(t)=0(dr/dt)<0 \quad (4)$$

In the remote control system of this modification, since the force sensor 5 is unnecessary, a similar effect to this embodiment can be attained with a simple configuration.

Moreover, also in this modification, the virtual reaction-force information generating module 23A may output the virtual reaction-force information P(t) illustrated in Equation (3).

Note that, although in this embodiment the case where the operating mode selected in the mode selector 25 is "the manual mode" is described, the operating mode selected in the mode selector 25 may be "the automatic mode." The motion controller 6 controls the operation of the slave arm 1 according to the given preset program without using the operational information sent from the master arm 2, when the operating mode in which the slave arm 1 is operated is "the automatic mode."

Moreover, the operating mode selected in the mode selector 25 may be "the correctable automatic mode." When the operating mode is "the correctable automatic mode," the motion controller 6 uses both the given program and the operational information. Note that, when the operating mode is "the correctable automatic mode," the motion controller 6 uses only the given program if the operational information has not been sent to the motion controller 6. In more detail, when the operating mode in which the slave arm 1 is operated is "the correctable automatic mode," the motion controller 6 controls the operation of the slave arm 1 using both the given program and the operational information, if the operational information is received while the slave arm 1 operates automatically using the given program. Thus, the slave arm 1 performs an operation corrected from the operation related to the given program, i.e., the operation which is to be performed automatically.

Note that, in this embodiment, although the motion controller 6 is configured so that the slave arm 1 is operated according to any one of operating modes, "the automatic mode," "the correctable automatic mode" and "the manual mode," which is selected by the operator using the mode selector 25 of the input device 9, the present disclosure is not limited to such a configuration. For example, the motion controller 6 may have an output controlling module (not illustrated) which outputs an inquiry about a permission to continue the automatic operation of the slave arm 1 to the operator when the motion controller 6 controls the slave arm 1 so that the slave arm 1 is operated in "the automatic mode" up to a given step, and a continuation determining module (not illustrated) which determines whether a continuation of the automatic operation is permitted based on an inputted signal received by a receiving module (not illustrated) after the output of the inquiry by the output controlling module (not illustrated). Thus, in a scene where the skilled operator is required, the operator is able to perform the work after switching the mode from "the automatic mode" to "the manual mode."

Note that, in this embodiment, although the remote control system 100 is applied to the work in which the component which has already been applied the lubricating oil (212) is mounted by another component, the present disclosure is not limited to this configuration. The remote control system 100 may be applied to, for example, a work to an object to be worked which is in liquid, or a stirring work of high-viscosity liquid, as long as the work requires high precision. It becomes easier to distinguish whether the object to be worked is in liquid by adding a viscous resistance to the force presented to an operating device.

Second Embodiment

Next, a second embodiment is described. A fundamental configuration of the remote control system of this embodiment is similar to that of the embodiment described above. Below, description of configurations common to those of the first embodiment is omitted, but different configurations are mainly described. The remote control system of this embodiment is applied to a surgical operation system, and the end effector is a surgical instrument. The surgical operation system is a master-slave type operation support robot. Here, it is a system in which an operator, such as a surgeon, performs an endoscope surgical operation to a patient.

Note that, since the surgical operation system of this embodiment is for operation support, the slave arm 1 is configured so as to operate only in "the manual mode." Thus, the input device 9 is not provided with the mode selector 25 for selecting the operating mode by the operator (see FIG. 3). The operator operates the operating part 26 of the master arm 2 while looking at the monitor 12 to operate the slave arm 1 as he/she intended. The operating part 26 may have a well-known configuration, as long as the operator is able to operate the operating part 26 to operate the slave arm 1. The slave arm 1 may also have a well-known configuration, as long as it is controllable according to the operational information outputted from the master arm 2. For example, the slave arm 1 has a configuration in which the tip-end part is movable in a three-dimensional space with respect to the base-end part.

Figure 6:
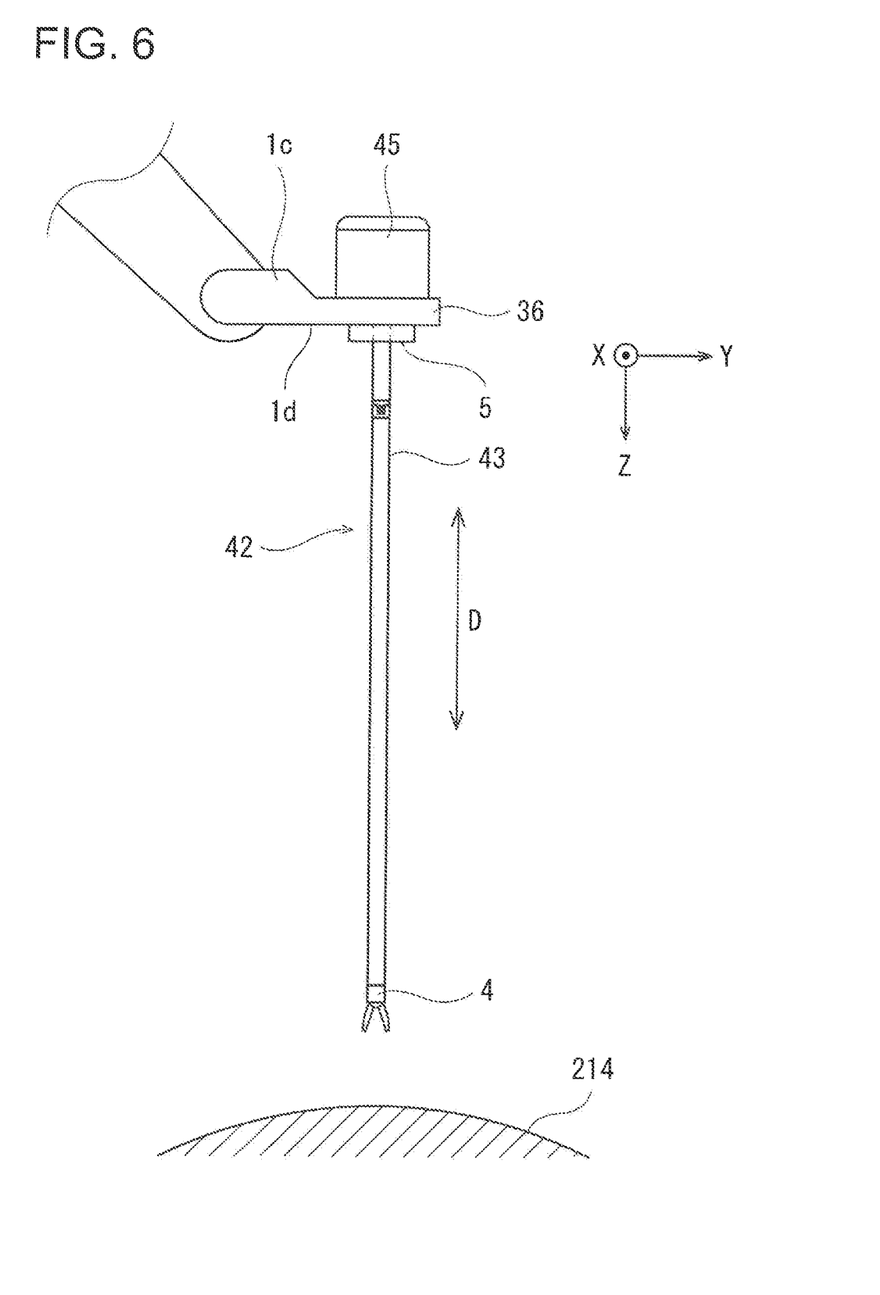
FIG. 6 is a schematic view illustrating a configuration of a robot system according to a second embodiment.

FIG. 6 is a schematic view illustrating a configuration of the remote control system of the robot according to the second embodiment. As illustrated in FIG. 6, a holder 36 (instrument holder) which holds an instrument (surgical instrument) 42 is formed in the hand part 1c at the tip end of the slave arm 1. The force sensor 5 is attached between the attachment surface 1d (a back surface of the holder 36) of the hand part 1c at the tip end of the slave arm 1, and the instrument 42. The instrument 42 is held attachably and detachably by the holder 36. A shaft 43 of the instrument 42 held by the holder 36 is configured so as to extend parallel with reference directions D. Note that an endoscope assembly may be held attachably and detachably by the holder 36. In this embodiment, the operator operates the instrument 42 of the slave arm 1 by the operation of the slave arm 1.

The instrument 42 is comprised of a drive unit 45 provided to a base-end part thereof, the end effector (surgical tool) 4 provided to a tip-end part thereof, and a long and narrow shaft 43 which connects between the drive unit 45 and the end effector 4. The reference directions D are defined in the instrument 42, and the drive unit 45, the shaft 43, and the end effector 4 are aligned in parallel with the reference directions D. The end effector 4 of the instrument 42 is selected from the group comprised of surgical instruments having operable joint(s) (e.g., forceps, scissors, and a grasper, a needle holder, a microdissector, a staple applier, a tucker, a siphonage tool, a snare wire, and a clip applier), and instruments without a joint (e.g., a cutting blade, a cauterize probe, a syringe, a washer, a suction orifice).

In the surgical operation system (100), various operations are performed to a patient 214 by the surgical instrument (4) at the tip end of the slave arm 1. Not only a general operation but the operation using the surgical operation system (100) also requires the skilled operator.

Figure 7:
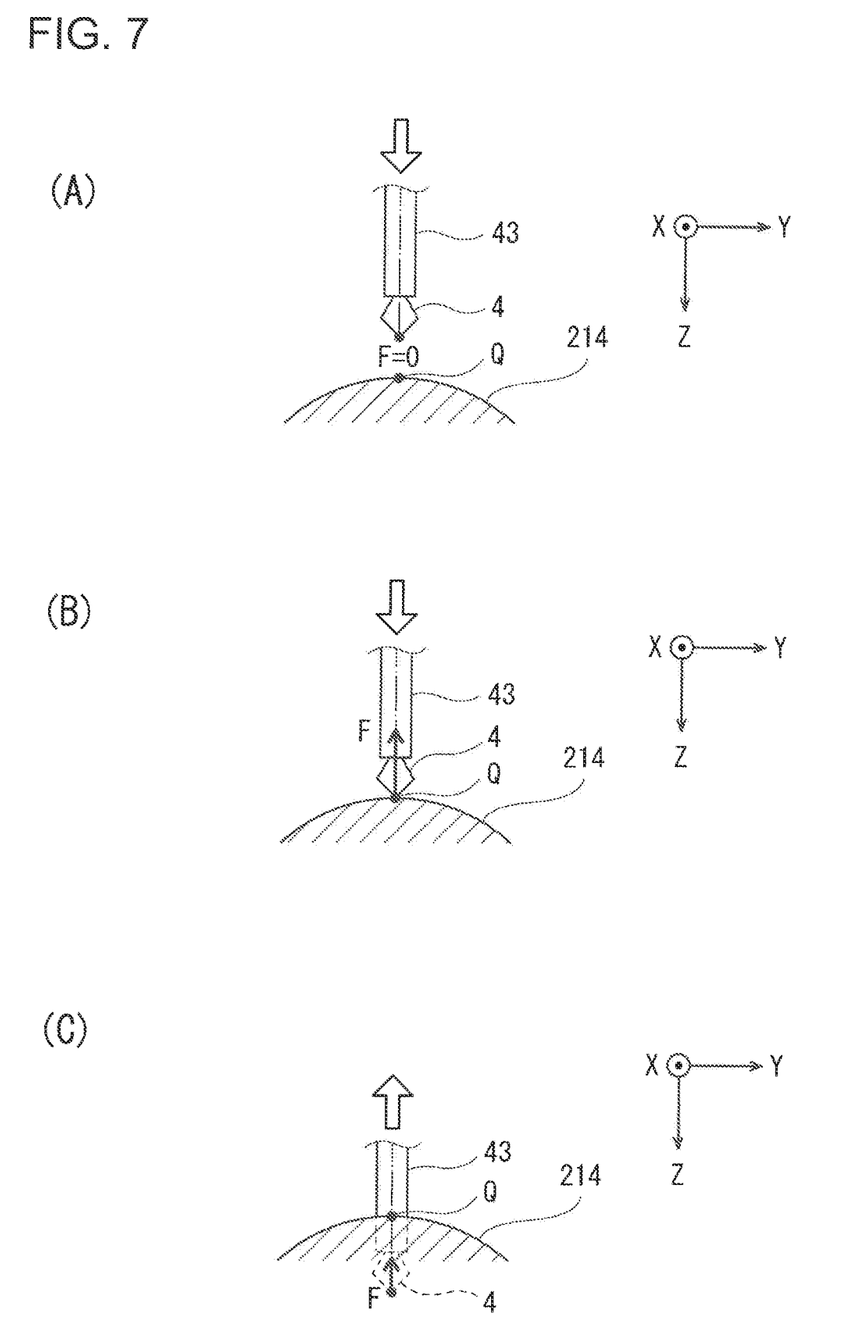
FIG. 7 is a view schematically illustrating a force acting on a tip end of a surgical instrument of FIG. 6 according to an operating stage.

FIG. 7 is a view schematically illustrating a force acting on the tip end of the surgical instrument (4) according to an operating stage. First, as illustrated in FIG. 7(A), the operator operates the master arm 2 (the operating part 26) while looking at the monitor 12 to depress the tip end of the surgical instrument (4) attached to the shaft 43 in a direction toward the patient 214 (in this figure, the positive Z-axis direction) by the operation of the slave arm 1. Here, for example, the tip end of the surgical instrument (4) is controlled so that it is located at an incising part Q of the patient 214. In this embodiment, a contact determination of whether the tip end of the surgical instrument (4) contacts the patient 214 is performed based on the detection signal of the force sensor 5. Since no force is applied to the tip end of the surgical instrument (4) until the tip end contacts the incising part Q, a force value detected by the force sensor 5 is zero.

Next, as illustrated in FIG. 7(B), when the tip end of the surgical instrument (4) contacts the incising part Q, the operator starts the operation with the surgical instrument (4) by the operation of the slave arm 1 by operating the master arm 2 while looking at the monitor 12. When the force sensor 5 attached to the tip end of the slave arm 1 detects the force applied to the tip end of the surgical instrument (4), the virtual reaction-force information generating module 23 determines whether the force F applied to the tip end of the surgical instrument (4) increases with time based on the detection signal of the force sensor 5. In FIG. 7(B), when the tip end of the surgical instrument (4) contacts the incising part Q of the patient 214, it receives a force in the negative Z-axis direction. In this case, since the force applied to the tip end of the surgical instrument (4) increases with time, the virtual reaction-force information generating module 23 outputs, as above Equation (1), the force information containing the first force component having the positive correlation to the velocity at the tip end of the surgical instrument (4), to the master arm 2 (the force applying device 28) as the virtual reaction-force information P(t). According to Equation (1), the first force component having the positive correlation to the velocity at the tip end of the robot hand (4) is a force component proportional to the velocity component at the tip end of the robot hand (4).

The force applying device 28 gives a force to the master arm 2 (the operating part 26) in order to make the operator perceive the force according to the virtual reaction-force information outputted from the virtual reaction-force information generating module 23. The operator is able to perceive the force according to the virtual reaction-force information given to the operating part 26. That is, the operator is able to operate the operating part 26 so as to cut the incising part Q of the patient 214 by the surgical instrument (4), while perceiving from the operating part 26 the virtual reaction force of which the viscous resistance is exaggerated. Therefore, a highly-precise work is possible.

Moreover, since the force applying device 28 gives the force to the operating part 26 in order to make the operator perceive the force according to the force information consisting of the first force component (see Equation (1)), the operating part 26 does not have a bad influence on its operability even if the operator removes his/her hand from the operating part 26 because the operating part 26 does not operate unintentionally.

On the other hand, as illustrated in FIG. 7(C), the operator may take out the once-inserted surgical instrument (4) from in vivo of the patient 214 during or after the operation. In this case, the tip end of the surgical instrument (4) receives a force in the minus Z-axis direction. The power F applied to the tip end of the surgical instrument (4) (in the negative Z-axis direction) decreases compared with the case of FIG. 7(B). As a result, since the force applied to the tip end of the surgical instrument (4) decreases with time, the virtual reaction-force information generating module 23 outputs the value of zero to the force applying device 28 of the master arm 2. As a result, the force applying device 28 does not give any force to the operating part 26. Since the operator does not perceive the viscous resistance from the operating part 26, a smooth operation is possible.

Note that, in this embodiment, although the virtual reaction-force information generating module 23 outputs the force information containing the first force component having positive correlation to the velocity at the tip end of the surgical instrument (4) as the virtual reaction-force information (see Equation (1)), the present disclosure is not limited to this configuration. The virtual reaction-force information generating module 23 may output the virtual reaction-force information P(t) illustrated in Equation (3) described above.

Note that, upon generating the second force component f(t) of Equation (3), the virtual reaction-force information generating module 23 converts the force applied to the tip end of the surgical instrument (4), which is detected by the force sensor 5, into an appropriate range, to set the force given to the operating part 26 as a force which falls within a range where the movement of the operating part 26 is permitted, when the operator removes his/her hand from the operating part 26.

Note that, in this embodiment, although the virtual reaction-force information generating module 23 outputs the value of zero when the force applied to the tip end of the surgical instrument (4) decreases (see Equation (1)), it may output the value of zero when an absolute value of the force is smaller than a given value.

Note that, as a modification of this embodiment, it may not be provided with the force sensor 5, similar to the configuration of the modification of the first embodiment (see FIG. 5). In this case, the virtual reaction-force information is generated only based on the velocity at the tip end of the surgical instrument (4). Since the force sensor 5 is unnecessary, similar effects to this embodiment can be obtained with a simple configuration.

Note that, in each of the embodiments, although the first force component having the positive correlation to the velocity at the tip end of the end effector 4 is the force component proportional to the velocity component at the tip end of the end effector 4 (see Equation (1)), it may be a force component, for example, proportional to a square of the velocity component, as long as it is a force component which increases according to the increase in the velocity component.

Other Embodiments

Note that, although the robot system 100 of each of the embodiments described above is comprised of the master-slave type remote control system, the present disclosure is not limited to this configuration. For example, it may be configured in other robot systems so that, when a work is performed by the end effector attached to the robot arm, surrounding persons or administrator(s) of the system perceive the virtual reaction force.

It is apparent for a person skilled in the art that many improvements and other embodiments of the present disclosure are possible from the description. Therefore, the above description is to be interpreted only as illustration, and it is provided in order to teach a person skilled in the art the best mode that implements the present disclosure. Details of one or both the structure and function can substantially be changed, without departing from the spirit of the present disclosure.

INDUSTRIAL APPLICABILITY

The present disclosure is useful when applying the robot system to the work which requires high precision.

DESCRIPTION OF REFERENCE CHARACTERS

1 Slave Arm (Robot Body)
2 Master Arm (Operating Device)
3 Control Device
4 End Effector
5 Force Sensor
6 Motion Controller
7 Force-sensing Information Processor
8 Monitor Controller
9 Input Device
10 Memory 20 Encoder
21 Position Calculating Module
22 Velocity Calculating Module
23 Virtual Reaction-force Information Generating Module
25 Mode Selector
26 Operating Part
27 Operational Information Generating Part
28 Force Applying Device
30 Current Sensor
100 Remote Control System
200 Fitting Component (Shaft)
210 Fitted Component (Gear)
211 Fitting Hole
212 Lubricating Oil
214 Patient

What is claimed is:

1. A robot system, comprising:
a robot body including a robot arm and an end effector attached to the robot arm;
an operating device, having an operating part and configured to output, when the operating part is operated, operational information according to the operation;
a motion controller configured to control operation of the robot body according to the operational information outputted from the operating device;
a velocity detector configured to detect a velocity at a tip end of the end effector;
a virtual reaction-force information generating module configured to output force information containing a first force component having a positive correlation to the velocity at the tip end of the end effector, as virtual reaction-force information; and
a force applying device configured to give a force to the operating part in order to make an operator perceive a force according to the virtual reaction-force information outputted from the virtual reaction-force information generating module.

2. The robot system of claim 1, wherein the robot body is a slave arm, the operating device is a master arm, and the slave arm is remotely controlled by the master arm.

3. The robot system of claim 1, wherein the virtual reaction-force information generating module outputs force information consisting of the first force component as the virtual reaction-force information.

4. The robot system of claim 1, wherein the virtual reaction-force information generating module determines whether the velocity at the tip end of the end effector is positive or negative, and outputs the virtual reaction-force information when the velocity at the tip end of the end effector is positive, and outputs a value of zero when the velocity at the tip end of the end effector is negative.

5. The robot system of claim 1, wherein the robot body includes a force detecting device configured to detect a force applied to the tip end of the end effector, and
wherein the virtual reaction-force information generating module outputs force information that is obtained by adding a second force component according to the force detected by the force detecting device to the first force component, as the virtual reaction-force information.

6. The robot system of claim 5, wherein the force detecting device is attached to a base end of the end effector, and is a force sensor configured to detect the force applied to the tip end of the end effector.

7. The robot system of claim 1, wherein the first force component is a force component proportional to the velocity at the tip end of the end effector.

8. The robot system of claim 1, further comprising a mode selector configured to select, as an operating mode of the motion controller in which operation of the robot body is controlled, any one of an automatic mode in which the operation of the robot body is controlled using a given preset program without reflecting the operational information on the operation of the robot body, a correctable automatic mode in which the operation of the robot body is controlled using the given preset program in the state where the operational information is reflectable on the operation of the robot body, and a manual mode in which the operation of the robot body is controlled using the operational information without using the given program,
wherein, when the operating mode is the correctable automatic mode, the motion controller controls the robot body so as to perform an operation corrected from the operation related to the given program in response to the operational information while the robot body operates using the given program.

9. (Surgical Operation System) The robot system of claim 1, wherein a remote control system of the robot is applied to a surgical operation system, and the end effector is a surgical instrument.

* * * * *